United States Patent

Burrell et al.

[11] 4,085,212
[45] Apr. 18, 1978

[54] PESTICIDAL DIHYDROTETRAZOLO [1,5-a] QUINAZOLINE COMPOUND AND PROCESSES AND COMPOSITIONS FOR USING THE SAME

[75] Inventors: Raymond Alexander Burrell, Camberley; John Michael Cos, Workingham, both of England

[73] Assignee: Imperial Chemical Industries Limited, London, England

[21] Appl. No.: 712,375

[22] Filed: Aug. 6, 1976

[30] Foreign Application Priority Data

Aug. 14, 1975 United Kingdom ............... 33931/75

[51] Int. Cl.² ...................... A01N 9/22; C07D 487/04
[52] U.S. Cl. .......................................... 424/251; 71/92; 260/256.4 F; 260/256.5 R
[58] Field of Search ...................... 260/256.4 F; 71/92; 424/251

[56] References Cited
U.S. PATENT DOCUMENTS

| 3,389,137 | 6/1968 | Mosby et al. | 260/256.4 F |
| 3,835,137 | 9/1974 | Wagner | 260/256.4 F |

OTHER PUBLICATIONS

Vereshchagina, et al., "Chemical Abstracts", vol. 61, 1964, col. 8307f.

*Primary Examiner*—Donald G. Daus
*Assistant Examiner*—James H. Turnipseed
*Attorney, Agent, or Firm*—Cushman, Darby & Cushman

[57] ABSTRACT

A dihydrotetrazolo[1,5-a]quinazoline compound which in free base form has the formula:

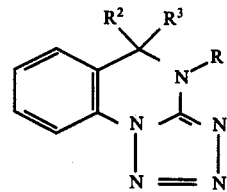

wherein $R^3$ is hydrogen, hydroxy or dialkylamino of from 1 to 4 carbon atoms; $R^2$ is dialkylamino when $R^3$ is dialkylamino and $R^2$ is hydrogen when $R^3$ is hydrogen or hydroxy; and R is a lower alkyl of from 1 to 4 carbon atoms. Pesticidal compositions containing such compound and prioceses for using the same to combat pests, especially fungi, are also disclosed.

6 Claims, No Drawings

PESTICIDAL DIHYDROTETRAZOLO [1,5-a] QUINAZOLINE COMPOUND AND PROCESSES AND COMPOSITIONS FOR USING THE SAME

This invention relates to pesticidal dihydrotetrazolo [1,5-a] quinazolines. More particularly, the invention relates to methods for combating pests, especially fungi, compositions therefor and to novel dihydrotetrazolo [1,5-a] quinazolines and processes for preparing them.

The present invention provides novel dihydrotetrazolo [1,5-a] quinazoline derivatives having the formula:

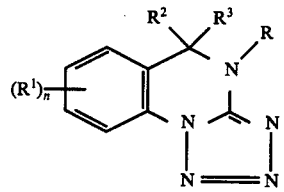

wherein $n$ is zero or an integer of 1 to 4 and each $R^1$ is selected from hydroxy, halogen, alkyl, alkoxy, alkylthio, alkylsulphonyl, nitro, amino, substituted amino, acyl, aroyl, cyano, carboxy or sulphonic acid or ester or amide; R is optionally-substituted alkyl or aryl; $R^2$ is hydrogen, or, when $R^3$ is other than hydrogen or hydroxy, di-substituted amino; $R^3$ is hydrogen, hydroxy, or di-substituted amino; and salts thereof.

In particular this invention provides the specific compounds having the structural formulae:

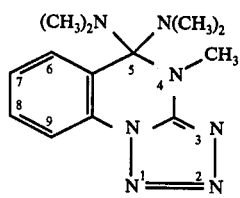

Compound No 1

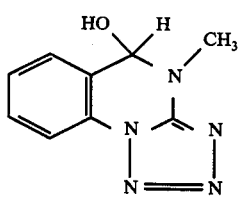

Compound No 2

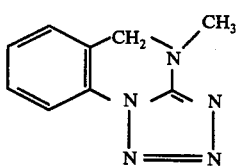

Compound No 3

In the first formula above is shown the numbering of the ring.

Preferred di-substituted amino groups for $R^2$ and $R^3$ are dialkylamino groups.

Preferred alkyl groups for $R^1$ and R are those containing from 1 to 4 carbon atoms, especially methyl.

These compounds may be prepared by the methods set out in Examples 1, 2 and 3 hereinafter, or by any obvious chemical variation thereof.

In so far as these methods are new, or are applied to the preparation of the novel compounds defined herein, they form part of the present invention.

The present invention further provides pesticidal compositions comprising as an active ingredient a dihydrotetrazolo [1,5-a] quinazoline derivative having the formula:

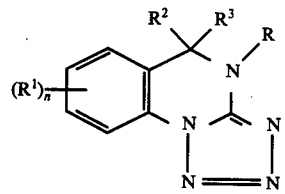

wherein $n$ is zero or an integer of 1 to 4 and each $R^1$ is selected from hydroxy, halogen, alkyl, alkoxy, alkylthio, alkylsulphonyl, nitro, amino, substituted amino, acyl, aroyl, cyano, carboxy or sulphonic acid or ester or amide; R is optionally substituted alkyl or aryl; $R^2$ is hydrogen, or, when $R^3$ is other than hydrogen or hydroxy, di-substituted amino; $R^3$ is hydrogen, hydroxy or di-substituted amino; or a salt thereof.

In a further aspect this invention provides pesticidal compositions comprising, as an active ingredient, the preferred, or specific, dihydrotetrazolo [1,5-a] quinazoline derivatives described above on pages 2 and 3.

The present invention further provides a process for combating fungi which comprises treating crops, plants, seeds, with a dihydrotetrazolo [1,5-a] quinazoline derivative having the formula:

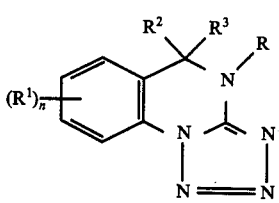

wherein $n$ is zero or an integer of 1 to 4 and each $R^1$ is selected from hydroxy, halogen, alkyl, alkoxy, alkylthio, alkylsulphonyl, nitro, amino, substituted amino, acyl, aroyl, cyano, carboxy or sulphonic acid or ester or amide; R is optionally substituted alkyl or aryl; $R^2$ is hydrogen, or, when $R^3$ is other than hydrogen or hydroxy, di-substituted amino; $R^3$ is hydrogen, hydroxy or di-substituted amino; or a salt thereof.

In a further aspect the invention provides a process as claimed in the preceding paragraph and wherein the dihydrotetrazolo [1,5-a] derivative is a preferred, or specific derivative as described above on pages 2 and 3.

In carrying the invention process into practical effect the pests, growing crops, plants, seeds, or soil, or any locus of any of the foregoing, may be treated by any of the well-known and established procedures used in agriculture and crop protection. Thus, for example, the active compound may be applied as solids, liquids, solutions, dispersions, emulsions and these may comprise, in addition to the active substance, any other adjuvant useful for formulation purposes, or any other biologically active substance, for example to increase the number of diseases combated.

Such solid or liquid substances and formulations may be applied, for example, by any conventional technique for example, by dusting, or otherwise applying the solid substances and formulations to the surfaces of growing crops, harvested produce, plants, seeds or soil, or to any part, or combination of parts thereof, or, for example, applying liquids or solutions for example, by dipping, spraying, mist blowing or soaking techniques.

The inventions process is therefore useful for treating plants, seeds, harvested fruits, vegetables, or cut flowers infested with, or liable to infestation with any of the aforementioned specific fungal or bacterial diseases.

The term "seeds" is intended to include propagative plant forms generally and therefore includes, for example, cut stems, corms, tubers, rhizomes and the like.

The active compounds, or salts thereof, may be used as such but are preferably formulated into compositions for this purpose. Preferred compositions contain, as an active ingredient, the compounds prepared as described in the Examples hereinafter.

The compositions of the invention may be in the form of dusting powders or granules wherein the active ingredient is mixed with a solid diluent or carrier. Suitable diluents or carriers may be, for example, kaolin, bentonite, kieselguhr, dolomite, calcium carbonate, talc, powdered magnesia, Fuller's earth, gypsum, Hewitt's earth, diatomaceous earth and china clay. Compositions for dressing seed, for example, may comprise an agent assisting the adhesion of the composition to the seed, for example, a mineral oil.

The compositions may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used in the process of the invention for plants or harvested produce which are generally solutions, aqueous dispersions or emulsions containing the active ingredient in the presence of one or more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example, sodium lauryl sulphate, salts of sulphonated aromatic compounds, for example, sodium dodecylbenzensulphonate, sodium, calcium or ammonium lignosulphonate, butylnaphthalene sulphonate, and a mixture of the sodium salts of diisopropyl- and triisopropylnaphthalene sulphonic acids. Suitable agents of the non-ionic type include, for example, the condensation products of ethylene oxide with fatty alcohols such as oleyl alcohols such as oleyl alcohol or cetyl alcohol, or with alkyl phenols such as octylphenol, nonylphenol and octylcresol.

Other non-ionic agents are the partial esters derived from long chain fatty acids and hexitol anhydrides, the condensation products of the said partial esters with ethylene oxide, and the lecithins. Suitable suspending agents are, for example, hydrophilic colloids, for example, polyvinylpyrrolidone and sodium carboxymethylcellulose, and the vegetable gums, for example, gum acacia and gum tragacanth.

The aqueous solutions, dispersions or emulsions may be prepared by dissolving the active ingredient in an organic solvent which may contain one or more setting, dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example, for improving the distribution, adhesive power and resistance to rain on treated surfaces, the different compositions can be better adapted for the various uses for which they are intended.

The compositions may also be conveniently formulated by admixing them with fertilizers. A preferred composition of this type comprises granules of fertilizer material incorporating an invention compound. The fertilizer material may, for example, comprise nitrogen, or phosphate-containing substances.

The compositions which are to be used in the form of aqueous dispersions or emulsions are generally supplied in the form of a concentrate containing a high proportion of the active ingredient, the said concentrate to be diluted with water before use.

The concentrates are often required to withstand storage for prolonged periods and after such storage, to be capable of dilution with water in order to form aqueous preparations which remain homogeneous for a sufficient time to enable them to be applied by conventional spray equipment.

The concentrates may conveniently contain from 4 – 85% and generally from 4 – 60% by weight of the active ingredient. A 20% aqueous solution is preferred. When diluted to form aqueous preparations, such preparations may contain varying amounts of the active ingredient depending upon the purpose for which they are to be used, but an aqueous preparation containing between 0.001% and 10% by weight of active ingredient may be used.

It is understood that the compositions of this invention may comprise, in addition to one or more active compounds according to the invention, one or more other substances having biological activity, for example, insecticidal, fungicidal, plant growth regulating, bactericidal or herbicidal activity.

This invention is illustrated, but not limited by, the following examples in which melting points and boiling points are given in degrees centigrade.

EXAMPLE 1

This example illustrates the preparation of 5,5-bis(dimethylamino)-4-methyl-4,5-dihydrotetrazolo[1,5-a]quinazoline having the structural formula:

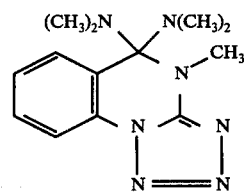

(Compound No 1)

A mixture of 4-methyl-4,5-dihydrotetrazolo[1,5-a]quinazolin-5-thione (3.3 g, prepared as described at the end of the present specific example), mercuric chloride (4.8 g) and N,N-dimethylformanide (45 ml) was stirred at room temperature for ten minutes, treated with dimethylamine (7.5 ml) and stirred for a further twenty hours. It was then diluted with water extracted with ether and the extracts washed well with water, dried and evaporated. The residue (2.6 g) was recrystallized from petroleum (b.p. 80°-100°) to give the title compound (2.1 g., m.p. 98°-100°).

The preparation of 4-methyl-4,5-dihydrotetrazolo[1,5-a]quinazolin-5-thione having the structural formula:

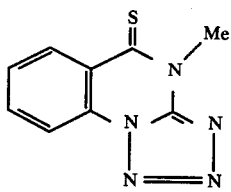

may be accomplished by any of the alternative procedures described below.

(a) A mixture of 4-methyl-4,5-dihydrotetrazolo[1,5-a]quinazolin-5-one (2.0 g, prepared as described in Example 2), phosphorus pentasulphide (4.8 g) and acetonitrile (100 ml) was refluxed for 28 hours, cooled, diluted with water (150 ml) and 2N hydrochloric acid (40 ml) and extracted with chloroform. The extracts were washed with 1N sodium hydroxide solution and water, dried and evaporated. The residue (2.2 g) was recrystallised from ethanol to give the title compound (0.72 g, m.p. 192°-194°).

OR (b) A mixture of 4-methyl-4,5-dihydrotetrazolo[1,5-a]quinazolin-5-one (20 g, prepared as described in Example 2), phosphorus pentasulphide (46.5 g), dichloroethane (1,1) and bromine (6 ml) was stirred at room temperature for 20 minutes, then refluxed for 4 hours, with vigorous stirring. The hot mixture was filtered through kieselguhr the solid washed with hot chloroform and the total filtrate cooled and washed with N sodium hydroxide solution (2 × 500 ml) and brine. The solution was dried and evaporated and the residue triturated with carbon disulphide to give the title compound (19.78 g, m.p. 193°-5°). Recrystallisation from chloroform raised the m.p. to 196°-7°.

OR (c) A mixture of 4-methyl-4,5-dihydrotetrazolo[1,5-a]quinazolin-5-one (200 mg), phosphorus pentasulphide (465 mg), mercuric chloride (270 mg), acetonitrile (1 ml) and dichloroethane (4 ml) was stirred at room temperature for 15 minutes, then refluxed for 90 minutes. It was filtered hot, the precipitate washed with hot chloroform and the total filtrates cooled, washed with N sodium hydroxide solution and brine, and dried. Evaporation and trituration of the residue with carbon disulphide gave the title compound (160 mg, m.p. 193°-6°).

EXAMPLE 2

This example illustrates the preparation of 5-hydroxy-4-methyl-4,5-dihydrotetrazolo[1,5-a]quinazoline having the structural formula:

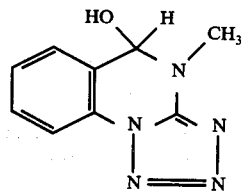

(Compound No 2)

A solution of 4-methyl-4,5-dihydrotetrazolo[1,5-a]quinazolin-5-one (400 mg., prepared as described at the end of the present specific example) in dry tetrahydrofuran (16 ml) was added slowly to a stirred suspension of lithium aluminum hydride (100 mg) in tetrahydrofuran (10 ml). The mixture was refluxed for 2 hours, cooled, treated with water and extracted with chloroform. The extracts were washed, dried and evaporated and the residue recrystallised from ethanol to give the title compound (60 mg., m.p. 210°-2°, decomp.).

The preparation of 4-methyl-4,5-dihydrotetrazolo[1,5-a]quinazolin-5-one having the structural formula:

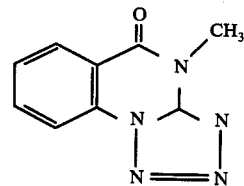

may be accomplished by any of the alternative procedures described below.

(a) A mixture of anthranilic acid (22.5 g), methyl isothiocyanate (12.5 g) and ethanol (200 ml) was refluxed for three hours, cooled and the precipitate filtered off and washed with water. Recrystallisation from ethanol gave 2-mercapto-3-methyl-3,4-dihydroquinazolin-4-one (13.0 g, m.p. 265°-266°). A mixture of this material (5.76 g) hydrazine hydrate (20 ml) and ethanol (30 ml) was refluxed for 30 minutes, then cooled. The precipitate was filtered off, washed with water and dried to give the 2-hydrazinoquinazolinone (3.16 g, m.p. 220°-223°). Recrystallisation from ethanol gave material m.p. 223°. A stirred solution of the crude product (1.9 g) in a mixture of hydrochloric acid (20 ml, 2N) and acetic acid (10 ml) was treated dropwise at 0°-5° with a solution of sodium nitrite (0.69 g) in water (5 ml). The mixture was allowed to attain room temperature and, after one hour, was filtered and the precipitate washed with water and dried to give the title compound (1.04 g, m.p. 164°-167°). Recrystallisation from ethanol gave material m.p. 167°.

OR (b) A solution of 4,5-dihydrotetrazolo[1,5-a]quinazolin-5-one (1.8 g, prepared as described in Example 1) in dry N,N-dimethylformamide (20 ml) was added slowly to a suspension of sodium hydride (0.5 g, 50% suspension in mineral oil, prewashed with light petroleum) in dimethyl-formamide (10 ml). After 10 minutes methyl iodide (5 ml) was added and the mixture allowed to stand for 3 hours. It was then diluted with water and the precipitate washed with water and dried to give the title compound (1.9 g, m.p. 164°-166°). Recrystallisation from ethanol gave material m.p. 167°.

OR (c) A mixture of methyl 2-isothiocyanatobenzoate (19.0 g, prepared as described in *J. Org. Chem.*, 1962, 27, 3701), sodium azide (9.85 g) and water (200 ml) was then refluxed, with stirring, for thirty minutes. It was then cooled, filtered through kieselguhr and acidified with dilute hydrochloric acid to give methyl 2(5'-mercaptotetrazol-1'-yl)benzoate (17.28 g, m.p. 147°–8°).

A mixture of this material (11.35 g), sodium hydride (2.12 g, 50% dispersion in mineral oil, prewashed with petroleum) and dry N,N-dimethylformamide (44 ml) was treated, with stirring at 0°, with N-methylchloroacetamide (5.24 g.). It was stirred for 18 hours, poured into ice-water and the precipitate filtered off and dried. Recrystallisation from methanol gave methyl 2[5'-(N-methyl-acetamidomethylthio)tetrazol-1'-yl]benzoate (8.52 g, m.p. 97°–8°).

A mixture of this material (7.0 g), acetic acid (58 ml), 2N sulphuric acid (58 ml) and potassium permanganate (5.8 g) was stirred at 5° for one hour, then decolorised by the addition of sodium metabisulphite. Water was added and the precipitate filtered off and washed with water. Recrystallisation from methanol gave methyl 2[5'-(N-methyl-acetamidomethanesulphonyl)tetrazol-1'-yl]benzoate (4.66 g, m.p. 138°–9°, decomp.).

A mixture of this material (3.4 g), 1,5-diazabicyclo-[4.3.0]non-5-one (1.2 g) and acetonitrile (28 ml) was refluxed for 30 minutes, cooled, diluted with water, acidified with dilute hydrochloric acid and extracted with chloroform. The extract was washed, dried and evaporated and the residue triturated with ether/petroleum and recrystallised from toluene to give methyl 2[5'-(N-acetyl-methylamino)tetrazol-1'-yl]benzoate (2.45 g, m.p. 134°).

A solution of this compound (275 mg) in hot methanol (3 ml) was rapidly cooled and treated, at 5°, with N sodium hydroxide solution (6 ml). After stirring for 5 minutes, the mixture was filtered and the filtrate extracted with chloroform. The aqueous layer was acidified with dilute hydrochloric acid to give 2(5'-methylaminotetrazol-1'-yl) benzoic acid (90 mg, m.p. 152°–4°).

A mixture of this compound (90 mg), ethanol (2 ml) and N hydrochloric acid (0.1 ml) was refluxed for 20 minutes and cooled to give the title compound (60 mg, m.p. 166°). It should be noted that this stage can also be catalysed by bases e.g. sodium hydroxide.

EXAMPLE 3

This example illustrates the preparation of 4-methyl-4,5-dihydrotetrazolo[1,5-a]quinazoline having the structural formula:

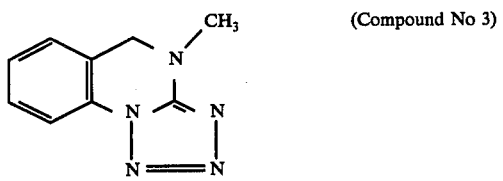

(Compound No 3)

A mixture of 3-methyl-1,2,3,4-tetrahydroquinazolin-2-thione (5.87 g., prepared as described in *J. Pharm. Sci.*, 1961, 50, 866), methyl iodide (6 ml) and ethanol (230 ml) was refluxed for 1 hour, cooled and diluted with ether. The precipitate (8.27g) was suspended in ethanol (42 ml), treated with hydrazine hydrate (42 ml) and the mixture refluxed for 1 hour, cooled, diluted with water and extracted with chloroform. The extracts were washed, dried and evaporated to give the 2-hydrazinoquinazoline (4.55g). This was dissolved in a mixture of 2N hydrochloric acid (27 ml.) and acetic acid (13 ml), cooled, and treated, dropwise below 5°, with a solution of sodium nitrite (2.04 g) in water (13 ml). The mixture was allowed to stand for a further hour at room temperature, basified with 10N sodium hydroxide solution and the precipitate filtered off and dried. Recrystallization from methanol gave the title compound (1.25 g., m.p. 134°–5°).

EXAMPLE 4

This example illustrates an atomisable fluid comprising a mixture consisting of 25% by weight of Compound No. 1 of Example 1 and 75% by weight of xylene.

EXAMPLE 5

This example illustrates a dusting powder which may be applied directly to plants or other surfaces and comprises 1% by weight of Compound No. 1 of Example 1 and 99% by weight of talc.

EXAMPLE 6

25 parts by weight of the product described in Example 1, 65 parts by weight of xylene, and 10 parts of an alkyl aryl polyether alcohol ('Triton' X-100; 'Triton' is a Trade Mark) were mixed in a suitable mixer. There was thus obtained an emulsion concentrate suitable for use in agriculture application.

EXAMPLE 7

5 parts by weight of Compound No. 1 of Example 1 were thoroughly mixed in a suitable mixer with 95 parts by weight of talc. There was thus obtained a dusting powder.

EXAMPLE 8

This example illustrates a concentrated liquid formulation in the form of an emulsion. The ingredients listed below were mixed together in the stated proportions and the whole stirred until the constituents were dispersed.

|  | % wt. |
|---|---|
| Compound No. 1 (Example 1) | 20 |
| "Lubrol" L ("Lubrol" is a Trade Mark) | 17 |
| Calcium dodecylbenzenesulphonate | 3 |
| Ethylene dichloride | 45 |
| "Aromasol" H ("Aromasol" is a Trade Mark) | 15 |
|  | 100% |

EXAMPLE 9

The ingredients listed below were ground together in the proportions stated to produce a powdered mixture readily dispersible in liquid.

|  | % wt. |
|---|---|
| Compound No. 1 (Example 1) | 50 |
| Dispersol T ("Dispersol" is a Trade Mark) | 5 |
| China Clay | 45 |
|  | 100% |

EXAMPLE 10

A composition in the form of grains readily dispersible in a liquid (for example water) was prepared by grinding together the first four of the ingredients listed below in the presence of water and then the sodium acetate was mixed in. The admixture was dried and passed through a British Standard mesh sieve, size 44 – 100 to obtain the desired size of grains.

|  | % wt. |
|---|---|
| Compound No. 1 (Example 1) | 50 |
| Dispersol T | 12.5 |
| Calcium lignosulphonate | 5 |
| Sodium dodecylbenzenesulphonate | 12.5 |
| Sodium acetate | 20 |
|  | 100% |

EXAMPLE 11

A composition suitable for use as a seed dressing was prepared by mixing all three of the ingredients set out below in the proportions stated.

|  | % wt. |
|---|---|
| Compound No. 1 (Example 1) | 80 |
| Mineral Oil | 2 |
| China Clay | 18 |
|  | 100% |

EXAMPLE 12

A granular composition was prepared by dissolving the active ingredient in a solvent, spraying the solution obtained onto the granules of pumice and allowing the solvent to evaporate.

|  | % wt. |
|---|---|
| Compound No. 1 (Example 1) | 5 |
| Pumice Granules | 95 |
|  | 100% |

EXAMPLE 13

An aqueous dispersion formulation was prepared by mixing and grinding the ingredients recited below in the proportions stated.

|  | % wt. |
|---|---|
| Compound No. 1 (Example 1) | 40 |
| Calcium lignosulphonate | 10 |
| Water | 50 |
|  | 100% |

The following constitutes an explanation of the compositions or substances represented by the various Trade Marks and Trade Names referred to in the foregoing Examples.

| | |
|---|---|
| "LUBROL" L | is a condensate of 1 mole of nonyl phenol with 13 molar proportions of ethylene oxide. |
| "AROMASOL" H | is a solvent mixture of alkylbenzenes. |
| "DISPERSOL" T | is a mixture of sodium sulphate and a condensate of formaldehyde with the sodium salt of naphthalene sulphonic acid. |
| "LISSAPOL" NX | is a condensate of 1 mole of nonyl phenol with 8 moles of ethylene oxide. |
| "TRITON" X-100 | is an alkyl aryl polyether alcohol. |

EXAMPLE 14

The compounds prepared according to Examples 1 to 3 were tested against a variety of foliar fungal diseases of plants. The technique employed is to spray the foliage of the undiseased plants with a solution of the test compound and also to drench the soil in which the plants are growing with another solution of the test compound.

All solutions for spraying contained 100 parts per million (ppm) of the test compound. All the soil drench solutions also contained 100 ppm of the test compound.

The plants were then infected with the disease it was desired to control and after a period of days, depending upon the particular disease, the extent of the disease was visually assessed. The results are given below, in the form of a grading as follows:

| Grading | Percentage Amount of Disease |
|---|---|
| 0 | 61 to 100 |
| 1 | 26 to 60 |
| 2 | 6 to 25 |
| 3 | 0 to 5 |
| 4 | 0 |

In the first Table below, the disease is given in the first column, whilst in the second column is given the time which elapsed between infecting the plants and assessing the amount of disease. The third column assigns to each disease a code letter, these code letters being used in the Second Table to identify the diseases.

TABLE

| Disease and Plant | Time interval (days) | Disease Code letter (Table No. 2) |
|---|---|---|
| Puccinia recondita (wheat) | 10 | A |
| Phytophthora infestans (tomato) | 3 | B |
| Plasmopara viticola (vine) | 7 | C |
| | 10 | |
| Piricularia oryzae | 7 | D |

TABLE

| Disease Code Letter | Compound and Disease Grading |
|---|---|
| A | 3(2) |
| B | 2(2) |
|  | 3(2) |
| C | 2(3) |
| D | 1(3) |
|  | 2(4) |
|  | 3(3) |

EXAMPLE 15

This Example illustrates the activity of the invention compounds and compositions against the soilborne fungal diseases *Rhizoctonia solani* and *Pythium ultimum*.

The test chemicals were prepared in the same way as for the foliar sprays and soil drench experiments of Example 14. They were then applied at the rate of 250 parts per million (ppm) to John Innes compost which had been inoculated 24 hours previously with spares of the fungal disease being tested against. Pots of 1½ inches diameter containing the inoculated soil and lettuce or mustard seeds were placed in 10 milliliters of the solution of the test chemical. After 7 to 8 days, seedling emergence was compared with that of a control pot placed in water alone. The results were graded on a scale 0 to 4 where 0 signifies no control of the disease and 4 signifies complete control.

TABLE

| Disease | Compound No. and Disease Grade (in parenthesis) |
|---|---|
| *Pythium ultimum* | 1 (1) |
| *Rhizoctonia solani* | 1 (1) |

EXAMPLE 16

Derivatives according to the invention were tested against general foliage-borne bacterial plant diseases in the glasshouse. The anti-bacterial screening method employs high humidity to aid infection of treated plants. The derivatives proved to have some activity as an antibacterial spray under these conditions.

Different experimental formulations were tested. The tests were carried out on fireblight of pears, rice blight and tomato spot.

Pear, tomato and rice seedlings were sprayed and/or root drenched with an aqueous solution containing 100 or 200 ppm of the test chemical. After 48 hours they were inoculated with the appropriate disease organism; *Erwinia amylovora* (fire blight) on pears, *Xanthomonas vesicatoria* (bacterial leaf spot) of peppers and *Xanthomonas oryzae* (rice blight) on rice. Inoculations were accompanied by wounding the plants which is necessary for bacterial infection to take place. Immediately afterwards the plants were placed under a mist propagator or in a humidity cabinet.

Symptoms were assessed on a 0 – 4 scale as shown below after up to 8 days.

| Grade | Percentage Amount of Disease |
|---|---|
| 0 | 61 – 100% |
| 1 | 26 – 60% |
| 2 | 6 – 25% |
| 3 | Up to 5% |
| 4 | Disease free plants |

Compound No. 2 gave a grading of 2 against *Pseudomonas tomato* and No. 3 a grading of 2 against *Xanthomonas oryzae*.

We claim:

1. A dihydrotetrazolo[1,5-a]quinazoline compound which in free base form has the formula:

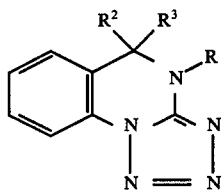

wherein $R^3$ is hydrogen, hydroxy or dialkylamino of from 1 to 4 carbon atoms; $R^2$ is dialkylamino of from 1 to 4 carbon atoms when $R^3$ is dialkylamino and $R^2$ is hydrogen when $R^3$ is hydrogen or hydroxy; and R is a lower alkyl of from 1 to 4 carbon atoms.

2. A quinazoline compound according to claim 1 and having the structural formulae:

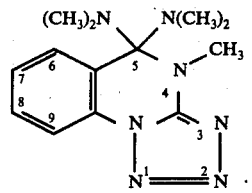

3. A quinazoline compound according to claim 1 and having the structural formula:

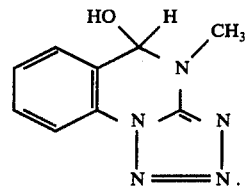

4. A quinazoline compound according to claim 1 and having the structural formula:

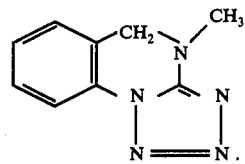

5. A pesticidal composition comprising as active ingredient, an effective amount of a quinazoline compound having in free base form the structural formula:

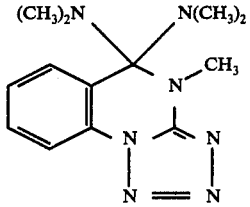

OR

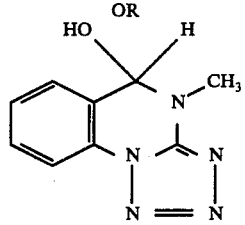

OR

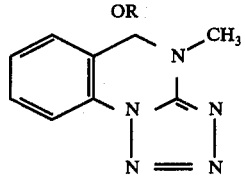

together with a carrier for said derivative.

6. A process for combating fungi which comprises subjecting said fungi to a fungicidally effective amount of a dihydrotetrazolo [1,5-a] compound which in free base form has the structural formula:
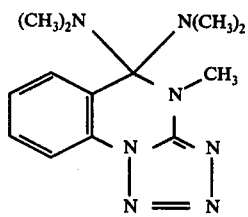
OR
-continued
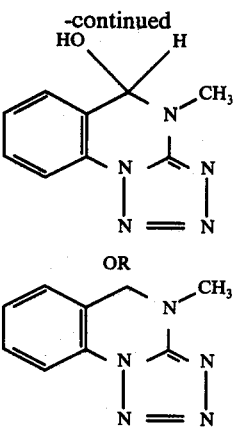
OR
* * * * *

UNITED STATES PATENT OFFICE
CERTIFICATE OF CORRECTION

Patent No. 4,085,212     Dated April 18, 1978

Inventor(s) Raymond Alexander BURRELL and John Michael COX

It is certified that error appears in the above-identified patent and that said Letters Patent are hereby corrected as shown below:

On the front page, Item [75] the second inventor's last name should be "Cox"

Signed and Sealed this

Twelfth Day of September 1978

[SEAL]

Attest:

RUTH C. MASON
*Attesting Officer*

DONALD W. BANNER
*Commissioner of Patents and Trademarks*